(12) United States Patent
Martin et al.

(10) Patent No.: US 9,523,671 B2
(45) Date of Patent: Dec. 20, 2016

(54) INDOXYL SULFATE AS A BIOMARKER OF PREBIOTIC EFFICACY FOR WEIGHT GAIN PREVENTION

(71) Applicant: Nestec S.A., Vevey (CH)

(72) Inventors: Francois-Pierre Martin, Vuisternens-devant-Romont (CH); Sebastiano Collino, Lausanne (CH); Ivan Montoliu Roura, Lausanne (CH)

(73) Assignee: NESTEC S.A. (CH)

( * ) Notice: Subject to any disclaimer, the term of this patent is extended or adjusted under 35 U.S.C. 154(b) by 0 days.

(21) Appl. No.: 14/774,651

(22) PCT Filed: Mar. 13, 2014

(86) PCT No.: PCT/EP2014/054912
§ 371 (c)(1),
(2) Date: Sep. 10, 2015

(87) PCT Pub. No.: WO2014/154493
PCT Pub. Date: Oct. 2, 2014

(65) Prior Publication Data
US 2016/0033473 A1    Feb. 4, 2016

(30) Foreign Application Priority Data
Mar. 28, 2013 (EP) .................................. 13161512

(51) Int. Cl.
*G01N 33/493* (2006.01)
*G01N 33/62* (2006.01)
(Continued)

(52) U.S. Cl.
CPC ........... *G01N 33/493* (2013.01); *A61K 31/702* (2013.01); *G01N 33/50* (2013.01); *G01N 33/62* (2013.01);
(Continued)

(58) Field of Classification Search
CPC ..................... G01N 2800/50; G01N 2800/044; G01N 33/50; G01N 33/6893; G01N 24/08; G01N 33/493; G01N 33/62; G01N 2570/00; G01N 2800/52; G01N 2800/70; A61K 31/702; C12Q 2565/633
See application file for complete search history.

(56) References Cited

U.S. PATENT DOCUMENTS 5,550,146 A    8/1996    Acosta et al.
7,993,931 B1   8/2011    Chen
(Continued)

FOREIGN PATENT DOCUMENTS

KR    20110052391 A    5/2011
WO    2004/074482 A1   9/2004
(Continued)

OTHER PUBLICATIONS

Zhu et al., "Quantitative profiling of tryptophan metabolites in serum, urine, and cell culture supernatants by liquid chromatography tandem mass spectrometry," Anal. and Bioanal. Chem., 401, 2011, 3249-3261.
(Continued)

*Primary Examiner* — Jennifer Wecker
(74) *Attorney, Agent, or Firm* — Kevin C. Hooper

(57) ABSTRACT

The present invention relates generally to the field of nutrition and health. In particular, the present invention relates to indoxyl sulfate as a biomarker in urine of the efficacy of prebiotics for the prevention of diet induced weight gain.

16 Claims, 3 Drawing Sheets

(51) Int. Cl.
  A61K 31/702 (2006.01)
  G01N 33/50 (2006.01)
  G01N 33/68 (2006.01)
  G01N 24/08 (2006.01)
(52) U.S. Cl.
  CPC ......... C12Q 2565/633 (2013.01); G01N 24/08 (2013.01); G01N 33/6893 (2013.01); G01N 2570/00 (2013.01); G01N 2800/02 (2013.01); G01N 2800/044 (2013.01); G01N 2800/50 (2013.01); G01N 2800/52 (2013.01); G01N 2800/60 (2013.01); G01N 2800/70 (2013.01)

(56) References Cited

U.S. PATENT DOCUMENTS

| | | | |
|---|---|---|---|
| 9,386,793 B2* | 7/2016 | Blaser | A61K 35/741 |
| 2006/0160237 A1 | 7/2006 | Du | |
| 2007/0043518 A1 | 2/2007 | Nicholson et al. | |
| 2009/0318556 A1* | 12/2009 | Idle | A61K 31/195 514/562 |
| 2015/0309051 A1 | 10/2015 | Martin et al. | |
| 2015/0362510 A1* | 12/2015 | Gall | G06F 19/3431 435/7.92 |

FOREIGN PATENT DOCUMENTS

| | | |
|---|---|---|
| WO | 2010/138899 A2 | 12/2010 |
| WO | 2012/024638 A2 | 2/2012 |
| WO | 2014/086603 A1 | 6/2014 |
| WO | 2014/086604 A1 | 6/2014 |
| WO | 2014/086605 A1 | 6/2014 |
| WO | 2014/154494 A1 | 10/2014 |

OTHER PUBLICATIONS

Svetkey et al., "Predictors of long-term weight loss in adults with modest initial weight loss, by sex and race," Obesity, 20, 2012, 1820-1828.
Marques-Quinones et al., "Adipose tissue transcriptome reflects variations between subjects with continued weight loss and subjects regaining weight 6 mo after caloric restriction independent of energy intake," Am. J. of Clinical Nutrition, 92, 2012, 975-984.
Patel et al., "The production of p-cresol sulfate and inoxyl sulfate in vegetarians versus omnivores," Clin. J. Am. Soc. Nephrology, 7, 2012, 982-988.
Rossi et al., "Pre-, pro-, and synbiotics: do they have a role in reducing uremic toxins? A systematic review and meta-analysis," Int. J. Nephrology, 2012, 2012, 1-20.
Lien et al., "The STEDMAN Project: Biophysical, Biochemical and Metabolic Effects of a Behavioral Weight Loss Intervention during Weight Loss, Maintenance, and Regain," OMICS: J. Integrative Biol., 13, 2009, 21-35.
International Search Report for PCT/EP2014/054912 dated Apr. 11, 2014.
Boulange, et al., "Early metabolic adaptation in C57BL/6 mice resistant to high fat diet induced weight gain involves an activation of mitochondrial oxidative pathways", J Proteome Res. Apr. 5, 2013;12(4):1956-68.
Dean, et al., "Glycine supplementation to low protein, amino acid-supplemented diets supports optimal performance of broiler chicks", Poult Sci. Feb. 2006;85(2):288-96.
Everard et al., "Responses of Gut Microbiota and Glucose and Lipid Metabolism to Prebiotics in Genetic Obese and Diet-Induced Leptin-Resistant Mice," Diabetes, 60, 2011, 2775-2786.
Gu, et al., "1H NMR metabolomics study of age profiling in children", NMR Biomed. Oct. 2009;22(8):826-33.
Jung et al, "1H NMR-based metabolite profiling of diet-induced obesity in a mouse mode", BMB reports by The Korean Society for Biochemistry and Molecular Biology, Dec. 2011, pp. 419-424.
Kim et al. "1H NMR-based metabolomic study on resistance to diet-induced obesity in AHAK knock-out mice", Biochem Biophys Res Commun. Dec. 17, 2010;403(3-4):428-34.
Kimura, et al., "Screening for fatty acid beta oxidation disorders. Acylglycine analysis by electron impact ionization gas chromatography-mass spectrometry", Journal of Chromatography B, 731, 1999, pp. 105-110.
Lloyd, et al., "Use of Mass spectrometry fingerprinting to identify urinary metabolites after consumption to specific foods", Am. J. Clin. Nutr. 2011: 94: pp. 981-991.
Newgard, et al., "A branched-chain amino acid-related metabolic signature that differentiates obese and lean human and contributes to insulin resistance", Cell Metabolism, Apr. 9, 2009, pp. 311-326.
Stella, et al., "Susceptibility of human metabolic phenotypes to dietary modulation", Journal of Proteome Research, 2006, 5; pp. 2780-2788.
Tomlinson et al., "Cannabinoid receptor antagonist-induced striated muscle toxicity and ethylmalonic-adipic aciduria in beagle dogs", Toxicological Sciences 192(2), 2012, pp. 268-279.
Trigg et al., "Addition of leucine precursors to the diet of leucine-starved mice," Am. J. Clin. Nutrition, 28, 1975, 947-949.
Zhen, et al., "Metabolomic and genetic analysis of biomarkers for peroxisome proliferator-activated receptor α expression and activation", Molecular Endocrinology 21(9), 2007 pp. 2136-2151.

* cited by examiner

INDOXYL SULFATE AS A BIOMARKER OF PREBIOTIC EFFICACY FOR WEIGHT GAIN PREVENTION

FIELD OF THE INVENTION

The present invention relates generally to the field of nutrition and health. In particular, the present invention relates to a method for predicting and/or quantifying the response of subjects to prebiotics in the prevention of diet induced weight gain, and to biomarkers which are useful in such a method.

BACKGROUND OF THE INVENTION

Obesity is a major public health issue as it enhances the risk of suffering several chronic diseases of increasing prevalence. Obesity results from an imbalance between energy intake and expenditure, associated with a chronic low-grade inflammation. It is known to contribute to the risk of developing type 2 diabetes mellitus (T2DM), non-alcoholic fatty liver disease (NAFLD), cancer, osteoarthritis and cardiovascular disease (CVD). Obesity results from a complex interaction between genetic and environmental factors, such as a high calorie diet, and lack of physical activity and recent research has also suggested that the gut microbiota may play a role in the development of obesity. An unbalanced diet rich in fat and/or carbohydrate is associated with triglyceride storage in adipose tissue, muscle, liver and the heart. Ectopic fat deposition, particularly in a central distribution, is also thought to contribute to a range of metabolic disorders such as hypertriglyceridaemia, hypertension, high fasting glucose and insulin resistance (IR).

Gut microbes are considered to contribute to body weight regulation and related disorders by influencing metabolic and immune host functions. The gut microbiota as a whole improves the host's ability to extract and store energy from the diet leading to body weight gain, while specific commensal microbes seem to exert beneficial effects on bile salt, lipoprotein, and cholesterol metabolism. The gut microbiota and some probiotics also regulate immune functions, protecting the host from infections and chronic inflammation. In contrast, dysbiosis and endotoxaemia may be inflammatory factors responsible for developing insulin resistance and body weight gain. In the light of the link between the gut microbiota, metabolism, and immunity, the use of dietary strategies to modulate microbiota composition is likely to be effective in controlling metabolic disorders. Although so far only a few preclinical and clinical trials have demonstrated the effects of specific gut microbes and prebiotics on biological markers of these disorders, the findings indicate that advances in this field could be of value in the struggle against obesity and its associated-metabolic disorders (Sanz et al. 2008).

Recent data, both from experimental models and from human studies, support the beneficial effects of particular food products with prebiotic properties on energy homeostasis, satiety regulation and body weight gain. Together, with data in obese animals and patients, these studies support the hypothesis that gut microbiota composition (especially the number of bifidobacteria) may contribute to modulate metabolic processes associated with syndrome X, especially obesity and diabetes type 2. It is plausible, even though not exclusive, that these effects are linked to the microbiota-induced changes and it is feasible to conclude that their mechanisms fit into the prebiotic effect. However, the role of such changes in these health benefits remains to be definitively proven. As a result of the research activity that followed the publication of the prebiotic concept 15 years ago, it has become clear that products that cause a selective modification in the gut microbiota's composition and/or activity(ies) and thus strengthens normobiosis could either induce beneficial physiological effects in the colon and also in extra-intestinal compartments or contribute towards reducing the risk of dysbiosis and associated intestinal and systemic pathologies (Roberfroid et al., 2010).

It would therefore be desirable to provide the art with a method that allows it to identify subjects early—ideally at risk—to put on weight (e.g. for instance after initiation of a weight loss program). In particular, it would be desirable to provide a method for predicting and/or quantifying the response of subjects to prebiotics in the prevention of diet induced weight gain, especially at an early stage after starting the administration of prebiotics.

Thus an object of the present invention is to provide a method that allows the early stratification of subjects according to whether or not they are likely to respond to a prebiotic-based intervention to prevent high fat diet induced or related weight gain.

SUMMARY OF THE INVENTION

Accordingly, the present invention provides a method for predicting and/or quantifying the response of a subject to prebiotics in the prevention of diet induced weight gain, comprising determining a level of indoxyl sulfate in a urine sample obtained from a subject that has consumed prebiotics, and comparing the subject's indoxyl sulfate level to a predetermined reference value, wherein a decreased indoxyl sulfate level, or an absence of change in the indoxyl sulfate level, in the urine sample compared to the predetermined reference value indicates that the administration of prebiotics is effective in the prevention of diet induced weight gain in the subject.

In one embodiment, the diet is a high fat diet.

In one embodiment, the method further comprises the steps of:

a) determining the level of at least one further biomarker selected from the group consisting of oxaloacetate, creatinine, trimethylamine, and alpha-keto-isovalerate in the urine sample, and b) comparing the subject's level of the at least one further biomarker to a predetermined reference value, wherein:

(i) a decreased oxaloacetate, creatinine, and/or alpha-keto-isovalerate level, or an absence of change in the oxaloacetate, creatinine, and/or alpha-keto-isovalerate level, in the urine sample; and/or (ii) an increased trimethylamine level, or an absence of change in the trimethylamine level, in the urine sample;

compared to the predetermined reference values indicates that the administration of prebiotics will be effective in the prevention of diet induced weight gain in the subject.

In one embodiment, the levels of the biomarkers in the urine sample are determined by $^1$H-NMR and/or mass spectrometry.

In one embodiment, the predetermined reference value is based on an average indoxyl sulfate level in urine in a control population of subjects consuming a high fat diet. In another embodiment, the predetermined reference value is the indoxyl sulfate level in urine in the subject before the prebiotics were consumed.

In one embodiment, the level of indoxyl sulfate and/or the further biomarkers are determined in a urine sample obtained from the subject after at least three consecutive days of prebiotic consumption. Preferably the subject has consumed the prebiotics in an amount of at least 2 g/day for this period or more.

In one embodiment, the prebiotic is selected from the group consisting of oligosaccharides, optionally containing fructose, galactose, mannose; dietary fibers, in particular soluble fibers, soy fibers; inulin; or mixtures thereof. Preferably the prebiotics are selected from the group consisting of fructo-oligosaccharides (FOS); galacto-oligosaccharides (GOS); isomalto-oligosaccharides; xylo-oligosaccharides; bovine milk oligosaccharides (BMOS); glycosylsucrose (GS); lactosucrose (LS); lactulose (LA); palatinose-oligosaccharides (PAO); malto-oligosaccharides (MOS); gums and/or hydrolysates thereof; pectins and/or hydrolysates thereof; and combinations thereof.

In a preferred embodiment, the prebiotics comprise galactooligosaccharides (GOS). In another preferred embodiment, the prebiotics comprise bovine milk oligosaccharides (BMOS), more preferably cow's milk oligosaccharides-galactooligosaccharides (CMOS-GOS). In another preferred embodiment the prebiotics comprise inulin and fructooligosaccharides (FOS).

In some embodiments, the subject is a mammal such as a human; a non-human species, including a primate; a livestock animal such as a sheep, a cow, a pig, a horse, a donkey, or a goat; a laboratory test animal such as a mouse, rat, rabbit, guinea pig, or hamster; or a companion animal such as a dog or a cat.

In one embodiment, the method is used to devise a stratified diet for a group of subjects or a personalized diet for the subject.

In a further aspect, the present invention provides a method for preventing diet-induced weight gain in a subject, comprising:
 a) performing a method as described above; and
 b) administering prebiotics to the subject if the level of indoxyl sulfate in the urine sample is decreased or unchanged compared to the predetermined reference value.

In one embodiment, administration of prebiotics to the subject is continued for at least one month.

In one embodiment, if the level of indoxyl sulfate in the urine sample is increased compared to the predetermined reference sample, prebiotics are not administered to the subject. Preferably an alternative treatment for weight gain prevention is provided to the subject, the treatment selected from calorie restriction, dietary fat intake reduction, a non-prebiotic weight loss product, or an exercise program.

In a further aspect, the present invention provides a biomarker in urine for predicting and/or quantifying the response of subjects to prebiotics in the prevention of diet induced weight gain, wherein the biomarker is indoxyl sulfate.

In a further aspect, the present invention provides use of indoxyl sulfate as a biomarker in urine for predicting and/or quantifying the response of subjects to prebiotics in the prevention of diet induced weight gain.

DETAILED DESCRIPTION OF THE INVENTION

Figure 1:
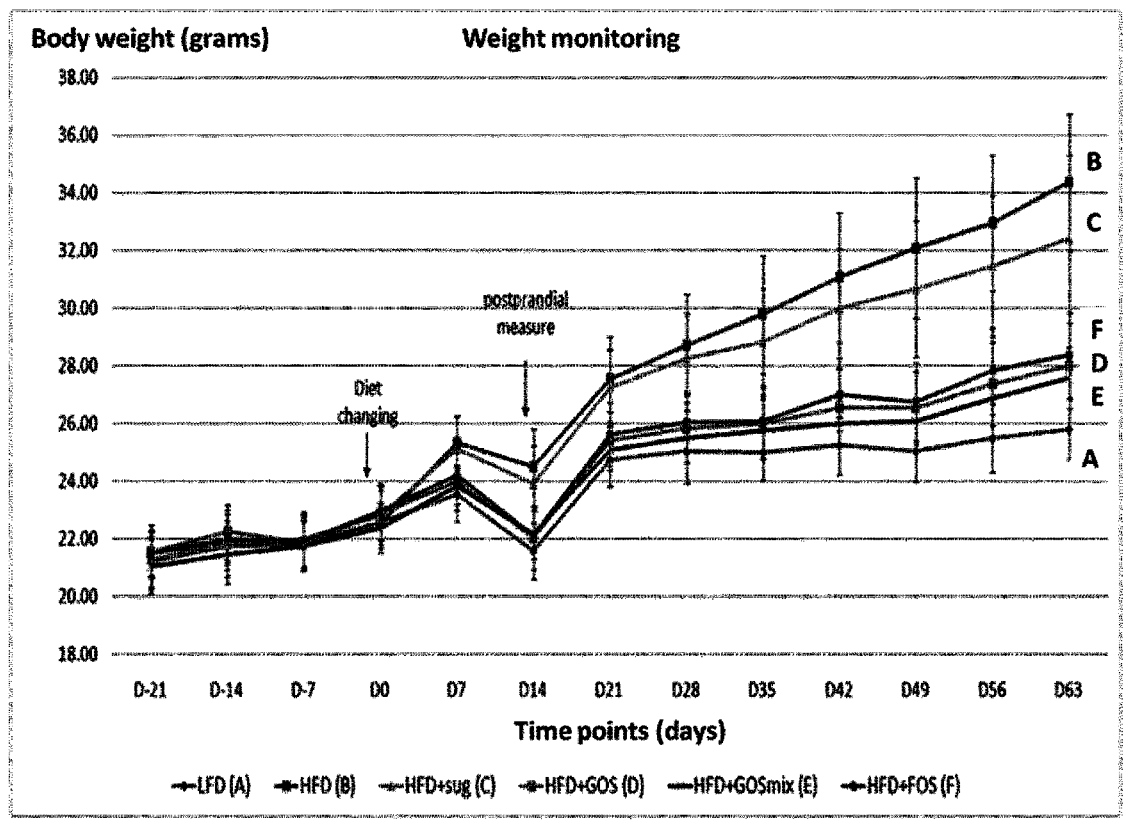
FIG. 1: Graph describing body weight curves for animals

The present inventors have used a metabonomics approach to achieve the objective of the present invention. Metabonomics is used to characterize the metabolic phenotype, which comprises the influence of various factors such as environment, drugs, dietary, lifestyle, genetics, and microbiome factors. Unlike gene expression and proteomic data that indicate the potential for physiological changes, metabolites and their dynamic concentration changes within cells, tissues and organs, represent the real end-points of physiological regulatory processes.

It is therefore a suitable approach to investigate the gradual metabolic changes linked to various dietary interventions and diseases development. Recently, metabolomics and lipidomics-based discoveries have been accelerating our understanding of disease processes, and will provide novel avenues for prevention and nutritional management of the sub-clinical disorders associated to metabolic syndrome. In particular, "omics" data have highlighted the contribution of energy metabolism (Krebs's cycle), lipid and amino acid processing, as well as inflammatory signals to the onset of obesity and IR.

Using a combination of proton nuclear magnetic resonance ($^1$H NMR) spectroscopy of urine samples collected overtime and weight gain monitoring, the inventors have identified novel metabolic biomarkers indicative of the efficacy of prebiotic intervention for weight gain prevention in a well defined C57BL/6 mouse model of diet induced obesity. The present inventors have characterised the gradual (e.g. on a weekly basis for a period of 13 weeks) metabolic adaptation of C57BL/6 mice fed with a high fat diet (HFD) with and without prebiotics using isocaloric diets. The inventors have established the specific metabolic signatures associated with gradual obesity development under different nutritional conditions, and phenotype variability within body weight gain dynamics.

By using a metabonomic approach, the inventors have shown that mitochondrial metabolic pathways (fatty acid β oxidation, branched-chain amino acid catabolism, butanoate metabolism, Nicotinamide Adenine Dinucleotide pathway and Krebs's cycle) are quickly up-regulated by high fat feeding which might reflect a fatty acid saturation of mitochondria and an impairment of energy metabolism. In addition, the metabonomic analysis showed a significant remodelling of gut microbial metabolism, as observed through changes in methylamines, dietary carbohydrate and protein fermentation.

The inventors could show that body weight gain was prevented in the groups of animals receiving a prebiotics-based intervention, and that the metabolic signatures associated to the difference in the body weight phenotype are associated with a specific modulation of high fat induced obesity dependent biological processes, including mitochondrial oxidative pathways (fatty acid β oxidation) and gut bacterial metabolism (methylamines, dietary carbohydrate and protein fermentation).

In particular, in the experiments described herein, mice fed with a HFD and prebiotics (GOS, CMOS-GOS and inulin/FOS) displayed a urinary decrease in indoxyl sulfate over time. The urinary decrease in indoxyl sulfate is strongly correlated with resistance to weight gain in the HFD-fed mice.

These results emphasize the role of mitochondria and gut microbiota in obesity development and show that the likelihood to respond beneficially to prebiotics in the prevention of diet induced weight gain can be determined from an early metabolic signature using a specific set of biomarkers defined herein.

The inventors were able to show that the urine metabolic response after one week on high fat feeding with any of the prebiotics (Day 7) enables the prediction of the final body weight gain for each individual (Day 70). The present method therefore allows the prediction and/or quantification of the response of animals to the dietary intervention at an early stage after initiation of prebiotic administration.

Predicting and/or Quantifying the Response of a Subject to Prebiotics

In one aspect, the present invention relates to a method of predicting and/or quantifying the response of a subject to prebiotics in the prevention of diet induced weight gain in the subject.

For instance, in one embodiment the method may be used to predict whether future or ongoing administration of prebiotics is likely to be effective in preventing weight gain. The method may thus be used, for example, to provide an indication of whether to continue with a prebiotic treatment for the prevention of weight gain, or whether to switch the subject to an alternative treatment scheme.

In an alternative embodiment, the method may be used to determine or quantify the effect of prior consumption of prebiotics by the subject. For instance the method may be used to provide an indication of whether prebiotic administration has prevented weight gain, in particular where this cannot be determined simply by determining the subject's weight. For example, within a specified test period it may not be known whether the subject would have gained or lost weight in the absence of prebiotic administration, particularly if the calorific value of the subject's diet is variable and/or unknown.

Subject

The method of the present invention may be carried out in subjects of any weight, in order to predict the efficacy of prebiotics in preventing diet-induced weight gain. Thus the subject may be an underweight, normal, overweight or an obese subject.

In particular in underweight, overweight or in obese subjects the method of the present invention may elucidate the genetic and metabolic predisposition of the subject towards weight gain. Based thereon, and ideally under further consideration of their general health status and lifestyle, personalized nutritional regimens may be developed that can help to maintain or regain a healthy status.

In one embodiment the subject to be tested is susceptible to diet-induced weight gain, particularly in the absence of prebiotic treatment. For instance, the subject may be an overweight or obese subject, for whom prebiotic administration is indicated in order to prevent weight gain. In some embodiments, the subject may be consuming a high fat diet, or a high calorie diet.

"Overweight" is defined for an adult human as having a BMI between 25 and 30. "Body mass index" or "BMI" means the ratio of weight in kg divided by the height in meters, squared. "Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30. "Normal weight" for an adult human is defined as a BMI of 18.5 to 25, whereas "underweight" may be defined as a BMI of less than 18.5.

A high fat diet may be defined as a diet from which the subject derives more than about 20% of its total calories from fat. In some embodiments, the high fat diet may contain more than about 30% of its total calories in fat. In other embodiments, the subject may derive more than about 40% of its total calories from fat.

Thus the actual fat content of a high fat diet may vary depending on the overall calorific value of the diet, as well as the gender, age, physical activity level, build, height and weight of the subject, for example. Typically for a 70 kg man with a moderate level of physical activity and a daily calorie intake of 2,700 kcal, a high fat diet may be considered to be the consumption of greater than 60 g fat per day (approximately 540 kcal energy value). Alternatively, a high fat diet in such a subject may be defined as in excess of 90 g fat/day (810 kcal/day) or 120 g fat/day (1080 kcal/day).

A high calorie diet may be defined as the consumption by the subject of greater than a recommended daily calorific intake, based for example on the gender, age, physical activity level, build, height and/or weight of the subject. For instance, a high calorie diet for a typical 70 kg man may be defined as the consumption of greater than 2,700 kcal/day, greater than 3,000 kcal/day, or greater than 3,500 kcal/day. For women, a high calorie diet may contain greater than 2,100 kcal/day, greater than 2,500 kcal/day, or greater than 3,000 kcal/day.

The subject tested in the method of the present invention has consumed prebiotics. Typically the subject has consumed prebiotics as part of a prescribed weight management program. For instance, a defined dose of prebiotics may be administered or supplied to the subject as a dietary supplement, in order to prevent weight gain.

Preferably the subject has consumed prebiotics for a period of at least one day, two days, three days, one week, two weeks, one month, two months or three months before the sample to be tested is obtained. In preferred embodiments, the sample is obtained between 3 and 14 days after initiating consumption of prebiotics, e.g. around 7 days after beginning prebiotic treatment. For instance, in some embodiments the subject has consumed prebiotics in an amount of at least 1 g/day, at least 2 g/day, at least 5 g/day or at least 10 g/day for the period defined above.

In one embodiment, the subject is a human. However, the method of the present invention is not limited to humans. It may also be used in non-human animals, for example in companion animals such as cats or dogs. Based thereon nutritional regimens may be designed that will contribute to a long life of the companion animal in good health.

In some embodiments, the subject is an infant or young child. The term "infant" refers to a child under the age of 12 months. The expression "young child" refers to a child aged between one and three years, also called a toddler. The infant can be a term or a preterm infant. A "preterm" or "premature" infant refers to an infant that was not born at term. Generally it refers to an infant born prior 36 weeks of gestation. In some embodiments the infant may be born by C-section, and/or a small for gestational age infant and/or a low birth weight infant. An "infant born by C-section" means an infant which was delivered by Caesarean section, i.e. an infant which was not vaginally delivered.

Prebiotics

A prebiotic is a non-digestible food ingredient than beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria.

Examples of prebiotics include certain oligosaccharides, such as fructooligosaccharides (FOS), galactooligosaccharides (GOS), isomalto-oligosaccharides, xylo-oligosaccharides, BMOs (bovine's milk oligosaccharide), glycosylsucrose (GS), lactosucrose (LS), lactulose (LA), palatinose-oligosaccharides (PAO), malto-oligosaccharides (MOS), gums and/or hydrolysates thereof, pectins and/or hydrolysates thereof, and any mixtures thereof. The BMOs can be selected from the list comprising N-acetylated oligosaccharides, sialylated oligosaccharides and any mixtures thereof. The BMOs can be "CMOS-GOS" (cow's milk oligosaccharides-galactooligosaccharides).

A combination of prebiotics may be used such as 90% GOS with 10% short chain fructo-oligosaccharides such as the product sold under the trademark Raftilose® or 10% inulin such as the product sold under the trademark Raftiline®.

A particularly preferred prebiotic is a mixture of galacto-oligosaccharide(s), N-acetylated oligosaccharide(s) and sialylated oligosaccharide(s) in which the N-acetylated oligosaccharide(s) comprise (represent) 0.5 to 4.0% of the oligosaccharide mixture, the galacto-oligosaccharide(s) comprise (represent) 92.0 to 98.5% of the oligosaccharide mixture and the sialylated oligosaccharide(s) comprise (represent) 1.0 to 4.0% of the oligosaccharide mixture. This mixture is hereinafter referred to as "CMOS-GOS". Preferably, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO2006087391 and WO2012160080 provide some examples of production of "CMOS-GOS".

"N-acetylated oligosaccharide" means an oligosaccharide having an N-acetyl residue. Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetyl-hexosamine or an N-acetylhexosamine containing oligosaccharide as described in Wrodnigg, T. M.; Stutz, A. E. (1999) Angew. Chem. Int. Ed. 38:827-828.

"Galacto-oligosaccharide" means an oligosaccharide comprising two or more galactose molecules which has no charge and no N-acetyl residue. Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1,4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

"Sialylated oligosaccharide" means an oligosaccharide having a sialic acid residue with associated charge. Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

In a particular preferred embodiment, the prebiotics comprise galactooligosaccharides (GOS). In another particularly preferred embodiment, the prebiotics comprise bovine milk oligosaccharides (BMOS), more preferably cow's milk oligosaccharides-galactooligosaccharides (CMOS-GOS). In another preferred embodiment the prebiotics comprise inulin and fructooligosaccharides (FOS).

Sample

The present method comprises a step of determining the level of indoxyl sulfate in a urine sample obtained from a subject.

Thus the present method is typically practiced outside of the human or animal body, i.e. on a body fluid (urine) sample that was previously obtained from the subject to be tested. Using urine as the body fluid to be tested has the advantage that it can be obtained regularly and non-invasively using a well-established procedure. The sample can also be obtained without the support of medical personnel.

Determining a Level of Indoxyl Sulfate in the Sample

The level of indoxyl sulfate in the sample can be detected and quantified by any means known in the art. For example, $^1$H-NMR, mass spectroscopy, e.g, UPLC-ESI-MS/MS, may be used. Other methods, such as other spectroscopic methods, chromatographic methods, labeling techniques, or quantitative chemical methods may be used as well. Preferably the indoxyl sulfate level in the sample and the reference value are determined by the same method.

Comparing the Indoxyl Sulfate Level to a Reference Value

The present method further comprises a step of comparing the subject's indoxyl sulfate level to a predetermined reference value.

The predetermined reference value may be based on an average indoxyl sulfate level in the tested body fluid in a control population, e.g. a population which has not consumed prebiotics. The control population can be a group of at least 3, preferably at least 10, more preferably at least 50 people with a similar genetic background, age and health status. Preferably the control population is a group of subjects who have consumed a similar diet to the subject to be tested, except in relation to prebiotics. Typically subjects in the control population have consumed a high fat diet, but have consumed no prebiotics or a level of prebiotics which is lower than that of the subject to be tested.

In another embodiment, the predetermined reference value is the indoxyl sulfate level in urine in the subject to be tested before the prebiotics were consumed. Thus the method may comprise monitoring a change in indoxyl sulfate levels in urine in the subject in response to consumption of prebiotics. For instance, in one embodiment a urine sample may be obtained from a subject in order to provide a reference value for the level of indoxyl sulfate, after which prebiotic treatment is initiated. Subsequently a further (test) urine sample may be obtained after a defined period of prebiotic consumption, as discussed above. The indoxyl sulfate level in the test sample is then compared to the reference sample in order to determine whether indoxyl sulfate levels in that subject have increased or decreased in response to the prebiotic treatment.

Determining Prebiotic Efficacy Based on Comparison of Indoxyl Sulfate Levels

In the present method, a decreased indoxyl sulfate level, or an absence of change in the indoxyl sulfate level, in the urine sample compared to the predetermined reference value indicates that the administration of prebiotics is effective in the prevention of diet induced weight gain. For example, the relative indoxyl sulfate levels in the test sample and reference sample may indicate whether prior consumption of prebiotics has been effective in preventing diet-induced weight gain, and/or whether further administration of prebiotics will be effective in preventing diet-induced weight gain.

In some embodiments, a decrease in the indoxyl sulfate level in the urine sample compared to the predetermined reference value is indicative of prebiotic efficacy. In particular, in embodiments where the reference value is based on an average indoxyl sulfate level urine in a control population of subjects consuming a high fat diet, the indoxyl sulfate level in the test sample is preferably decreased compared to the reference value. Also in embodiments where the reference value is based on the indoxyl sulfate level in urine in the subject before the prebiotics were consumed, the indoxyl sulfate level in the test sample is preferably decreased compared to the reference value.

Preferably the indoxyl sulfate level in the urine sample is decreased by at least 1%, 5%, at least 10%, at least 20%, at least 30%, or at least 50% compared to the predetermined reference value.

In other embodiments, an absence of change in the indoxyl sulfate level in the urine sample compared to the predetermined reference value may be indicative of prebiotic efficacy. For instance, in some embodiments the fat content and/or calorific value of the subject's diet may be variable. For instance, the fat content and/or calorific value of the subject's diet may increase between a time at which a control sample is taken to determine the reference value, and a later time at which the test sample is taken. In such embodiments, an absence of change in the indoxyl sulfate level in the test urine sample compared to the predetermined reference value may also be indicative of prebiotic efficacy.

Preferably an "absence of change in the indoxyl sulfate level" means a difference of less than 10%, less than 5%, less than 4%, less than 3%, less than 2% or less than 1% between the indoxyl sulfate level in the urine sample and the predetermined reference value.

Since in embodiments of the present invention a non-increased indoxyl sulfate level in the urine sample compared to the predetermined reference value indicates that the administration of prebiotics is effective in the prevention of diet induced weight gain, an increased level of indoxyl sulfate in the urine sample compared to the predetermined reference values may indicate that administration of prebiotics is less likely to be effective in the prevention of high fat diet induced weight gain. For instance, an increased level of indoxyl sulfate in the urine sample compared to the reference value may indicate that prior consumption of prebiotics has not been effective in preventing diet-induced weight gain, and/or that further administration of prebiotics will be ineffective in preventing diet-induced weight gain.

Further Biomarkers

In the present method, further biomarkers can also be used for predicting and/or quantifying the response of the subject to prebiotics in the prevention of diet induced weight gain.

As such the inventors have identified that non-increased urine concentrations of oxaloacetate, creatinine, and/or alpha-keto-isovalerate level allow the diagnosis of an increased likelihood to resist high fat diet induced weight gain. Furthermore, the present inventors have shown that an increased urine concentration of trimethylamine in urine is indicative of prebiotic efficacy in the prevention of diet induced weight gain The method of the present invention may, therefore, further comprise the steps of determining the level of at least one further biomarker selected from the group consisting of oxaloacetate, trimethylamine, creatinine, and alpha-keto-isovalerate in the urine sample, and comparing the subject's level of the at least one further biomarker to a predetermined reference value, wherein (i) a decreased oxaloacetate, creatinine, and/or alpha-keto-isovalerate level, or an absence of change in the oxaloacetate, creatinine, and/or alpha-keto-isovalerate level, or (ii) an increased trimethylamine level, or an absence of change in the trimethylamine level, in the urine sample compared to the predetermined reference values indicates that the administration of prebiotics is effective in the prevention of diet induced weight gain in the subject.

The further biomarkers may also be detected and quantified by $^1$H-NMR or mass spectroscopy, e.g., UPLC-ESI-MS/MS. Other methods, such as other spectroscopic methods, chromatographic methods, labeling techniques, or quantitative chemical methods may be used as well.

Preferably all of the biomarkers to be determined are assessed by the same technology. In some embodiments all of the tested biomarkers are assessed simultaneously.

The method of the present invention may comprise the assessment of at least 2, at least 3, at least 4, or at least 5 biomarkers as mentioned above.

For example, indoxyl sulfate may be assessed together with oxaloacetate.

Indoxyl sulfate may also be assessed together with trimethylamine.

Indoxyl sulfate may also be assessed together with creatinine.

Indoxyl sulfate may also be assessed together with alpha-keto-isovalerate.

Indoxyl sulfate may also be assessed together with oxaloacetate and trimethylamine.

Indoxyl sulfate may also be assessed together with oxaloacetate and creatinine.

Indoxyl sulfate may also be assessed together with oxaloacetate and alpha-keto-isovalerate.

Indoxyl sulfate may also be assessed together with trimethylamine and creatinine.

Indoxyl sulfate may also be assessed together with trimethylamine and alpha-keto-isovalerate.

Indoxyl sulfate may also be assessed together with creatinine and alpha-keto-isovalerate.

Indoxyl sulfate may also be assessed together with oxaloacetate, trimethylamine and creatinine.

Indoxyl sulfate may also be assessed together with oxaloacetate, trimethylamine and alpha-keto-isovalerate.

Indoxyl sulfate may also be assessed together with oxaloacetate, creatinine, and alpha-keto-isovalerate.

Indoxyl sulfate may also be assessed together with creatinine, trimethylamine, and alpha-keto-isovalerate.

Indoxyl sulfate may also be assessed together with oxaloacetate, trimethylamine, creatinine, and alpha-keto-isovalerate.

The advantage of assessing more than one biomarker is that the more biomarkers are evaluated the more reliable the diagnosis may become. For instance, if more than 1, 2, 3, 4 or 5 biomarkers are increased or decreased in level between the urine sample and the corresponding predetermined reference values, this may be more strongly indicative of whether or not prebiotics are likely to be effective in the prevention of diet induced weight gain in the subject.

The reference value for indoxyl sulfate and optionally for the further biomarkers is preferably measured using the same units used to characterize the level of indoxyl sulfate and optionally the further biomarkers obtained from the test subject. Thus, if the level of indoxyl sulfate and optionally the other biomarkers is an absolute value (e.g. the units of indoxyl sulfate are measured in μmol/l (μM)) the reference value is also preferably measured in the same units (e.g. μmol/l (μM) indoxyl sulfate in individuals in a selected control population of subjects or in the subject before administration of prebiotics).

The reference value can be a single cut-off value, such as a median or mean. Reference values of indoxyl sulfate and optionally the further biomarkers in obtained urine samples, such as mean levels, median levels, or "cut-off" levels, may be established in some embodiments by assaying a large sample of individuals in the general population or the selected population (e.g. individuals consuming a high fat diet). A statistical model, such as the predictive value method, may be used for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics, William and Wilkins, Harual Publishing Co. Malvern, Pa., which is incorporated herein by reference. The reference values for comparison in relation to a specific subject and biomarker may be selected according to the gender, race, genetic heritage, health status or age of the subject, for example.

Preventing Diet-Induced Weight Gain

In one aspect, the present invention provides a method for preventing diet-induced weight gain in a subject. The method may comprise performing a method as described above in order to determine prebiotic efficacy in the subject, and subsequently administering prebiotics or not depending on whether the method indicates that prebiotics are likely to be effective. In this way, prebiotic treatment can be targeted at subjects who are most likely to benefit, whereas an alternative weight gain prevention program can be developed for subjects in whom prebiotics are less likely to be effective.

In particular, the present method permits the early stratification of subjects, for example after a short term nutritional intervention with prebiotics. For instance the method may be performed after 1 week or less of prebiotic treatment, before the subject has put on weight which may result in health risks, to assess the efficacy of the intervention for long term body weight gain prevention. By determining whether the subject is susceptible to prebiotic based intervention to prevent diet induced weight gain, the lifestyle and/or diet of the subject can be adjusted accordingly at an early stage of the intervention process. Thus the method may be used in order to develop a personalized nutritional and/or exercise regime to provide a healthy physique for the subject.

Thus in embodiments of the present method, if the level of indoxyl sulfate in the urine sample is decreased or unchanged compared to the predetermined reference value, prebiotics are administered to the subject. Since the subject has typically already consumed prebiotics as part of the intervention process before the testing step, this may mean that the administration of prebiotics to the subject is continued. Optionally the levels of the further biomarkers described above may also be taken into account in determining whether to continue prebiotic administration.

The consumption of prebiotics by the subject may be continued in any amount, for instance the amount of prebiotics consumed may increase, decrease or stay the same after the testing step. However, after a positive indication of prebiotic efficacy is obtained, prebiotics are preferably administered to the subject in an amount at least equal to that consumed before the test sample is taken, e.g. in an amount of at least 2 g/day. The administration of prebiotics to the subject may be continued for at least one further week, at least 2 weeks, at least 1 month, at least 3 months, at least 6 months, at least 1 year or indefinitely after the determination of prebiotic efficacy.

Typically if a negative determination of prebiotic efficacy is obtained (as indicated by e.g. an increased indoxyl sulfate level, and optionally a decreased trimethylamine level and/or an increased level of one or more of the other biomarkers defined above), prebiotics are not administered to the subject. This may mean that prebiotic administration to the subject is discontinued, or at least not further prescribed to the subject as part of a managed nutritional regime. Typically in the event of an indication of lack of efficacy of prebiotics, prebiotic consumption by the subject may be decreased by at least 50%, at least 75% or at least 90% compared to the amount of prebiotics consumed before the test sample is taken. For instance, in some embodiments the subject may consume prebiotics in an amount of less than 2 g/day, less than 1 g/day, or less than 0.5 g/day after prebiotics are found to be ineffective.

In preferred embodiments, if the method indicates that prebiotics are likely to be ineffective then an alternative weight management strategy may be adopted for the subject. For instance, for such subjects it may be more beneficial to focus on well-established weight gain prevention methods such as dietary calorie restriction, dietary fat intake reduction or increased exercise. In other embodiments an alternative (non-prebiotic) weight loss product may be administered to the subject.

Preventing Obesity-Related Disorders

In some embodiments, an increased likelihood to respond to prebiotics in the prevention of diet induced weight gain may be indicative of a decreased risk of developing disorders associated with obesity and/or being overweight. Disorders associated with excess weight and/or obesity may be cardiovascular conditions such as atherosclerosis, stroke and heart disease and/or metabolic deregulations including diabetes. In particular, the risk of developing such weight-related conditions may be decreased in subjects who are both responsive to prebiotics and who continue to consume prebiotics in the long term, for instance as part of a managed nutritional regime. Conversely, subjects who are shown to be non-responsive to prebiotics in the prevention of weight gain may be at particular risk of developing these conditions, and require further or alternative nutritional or lifestyle-based interventions.

Further Aspects

In a further aspect, the present invention provides indoxyl sulfate as a novel biomarker in urine of prebiotic efficacy in the prevention of diet induced weight gain.

The invention also provides the use of indoxyl sulfate as a biomarker in urine for predicting and/or quantifying the response of subjects to prebiotics in the prevention of diet induced weight gain.

The study presented in this application provides an insight into the physiological mechanisms related to HF (high fat) induced obesity development and particularly highlights the specific metabolic adaptations associated to obese phenotype variability. The study also investigated, using isocaloric and carbohydrate match-content, the role of dietary soluble fibers on diet induced weight gain.

High fat ingestion provokes a rapid and consistent up-regulation of mitochondrial metabolic pathways resulting in more production of energy and increased mitochondrial fatty acid saturation. The metabolic signatures associated to the difference in the body weight phenotype are associated with a specific modulation of high fat induced obesity dependent biological processes, including mitochondrial oxidative pathways (fatty acid β oxidation) and gut bacterial metabolism (methylamines, dietary carbohydrate and protein fermentation).

Body weight gain was prevented in the groups of animals receiving any of the prebiotics based intervention, with a specific modulation of metabolic signatures ascribed to diet induced weight gain. The modulated metabolic signatures enabled an accurate prediction of final body weight gain and therefore the assessment of the efficacy of prebiotics to prevent weight gain.

The present inventors showed that the observed metabolic signature after only one week of intervention enables the prediction of final body weight gain at the end of the long term intervention (70 days). These results emphasize the role of mitochondria and gut microbiota in obesity development and indicate that responsiveness to prebiotics in the prevention of diet induced weight gain can be determined from an early metabolic signature using the biomarkers described herein.

The metabolic signature encapsulates contributions from both host energy metabolism and gut microbiota metabolic features. Consequently, this comprehensive analysis of the mechanisms underlying heterogeneous adaptation to high fat feeding provides novel and promising perspectives for weight management programs and personalized nutritional solutions.

The invention will now be described by way of example only with respect to the following specific embodiments.

Examples

Animal Handling Procedure and Sample Preparation

The experiment was carried out under appropriate national guidelines at the Nestle Research Center (NRC, Switzerland). The mice were maintained in individual cage under 12 h-12 h of light-dark regime and fed ad libitum during the overall experiment. After a period of acclimatization of three weeks on low fat diet (Research Diets, USA), the animals were switched to one of the following treatments, whilst one control group will be kept on low fat diets. A total of 90 C57BL/6 mice firstly received a standard chow diet for three weeks. Animals were randomized based on fasting blood glucose and body weight gain. At day 0, mice were then split in 6 groups of 15 animals, one group received a standard chow diet while the other groups received a high fat diet supplemented with prebiotics or sugars.

The low fat and high fat diets were obtained from standard low and high fat diets from Research Diets, USA, and were isocaloric (4057 Kcal/Kg):

Diet D09072901i is a Rodent Diet With 60 kcal % Fat

Diet D09072902i is a Rodent Diet With 60 kcal % Fat and 211 g Fiber Mix A

Diet D09072903i is a Rodent Diet With 60 kcal % Fat and 140 g Fiber Mix B

Diet D09072904i is a Rodent Diet With 60 kcal % Fat and 100 g Fiber Mix C

Diet D09072905i is a Rodent Diet With 60 kcal % Fat and 35.1 g Dextrose, 32.3 g Lactose and 1.45 g galactose The preparation of the diets was as described here below:

For mix A: GOS prebiotics

Add to diet 211 g of syrup or 158.2 g of dried powder, for a total of 531 Kcal.

In dry matters, 90 g are fibers (258Kcal), and 68.2 gm are sugars (272.8 Kcal),

To maintain isolcaloric balance between the different diets in the different groups, 258Kcal were removed from Maltodextrin, and 272.8Kcal from sucrose.

For mix B: GOS-CMOs prebiotics

Add to diet 140 g of powder, for a total of 350 Kcal.

In dry matters, 35.7 g are fibers (71.4Kcal), and remaining 278.6Kcal are from Sugars.

To maintain isolcaloric balance between the different diets in the different groups, 75Kcal were removed from maltodextrin, and 275Kcal from sucrose.

For mix C: Inulin and fructooligosaccharides (FOS)—Prebio 1

For 100 g product, add 30 g of product FOS to 70 gm of Inulin.

Add to diet 100 g of mix C.

In dry matters, 90 g are fibers (116Kcal), and 10 g are sugars (40Kcal).

To maintain isolcaloric balance between the different diets in the different groups, 116Kcal were removed from maltodextrin, and 40Kcal from sucrose.

For mix D:

Mix D is composed at 51% by glucose, 47% by lactose and 2% by galactose.

Add to diet, 68.75 g of Mix D, i.e. 275Kcal. (35 gm glucose, 32.3 gm lactose, 1.45 gm galactose)

To maintain isolcaloric balance between the different diets in the different groups, 275Kcal were removed from sucrose.

During the experimental study, the animals were monitored for their body weight and composition, food and water consumption. Difference in weight gain was assessed by non parametric test (Wilcoxon-Mann-Whitney U test).

There is a significant decrease in weight gain of animal received high fat diet in combination with prebiotics when compared to animals fed on high at diet of FI overtime.

Urine samples were collected on a weekly basis, namely the three weeks before diet switch (D-21 to D0) and 10 weeks during the nutritional interventions (D0 to D70). All the samples were snap-frozen at −80 C until analysis.

$^1$H NMR Spectroscopy

A volume of 40 µl of urine were diluted in 20 µl of buffer solution (NaHPO$_4$, 0.6M pH=7) containing sodium azide (3 mM) and TSP (0.5 mM). After centrifugation, samples were transferred in 1.7 mm diameter NMR tubes by using a syringe. $^1$H NMR spectra were then recorded on 600.13 MHz spectrometer, by performing 64 scans of a standard sequence with 64K data-points. The temperature of NMR experiment was maintained at 300 K. Processing of urine spectra was carried out by using the software TOPSPIN 2.0 (Bruker Biospin, Rheinstetten, Germany). For each spectrum, the FIDs were multiplied by an exponential function corresponding to a line broadering of 1 Hz, prior to being transformed into spectrum by a Fourrier Transformer. The phase and baseline of the spectra were then manually corrected. The chemical shift was calibrated by using the TSP signal at δ 0.0. Spectral assignments were achieved by using STOCSY (Statistical TOtal Correlation SpectroscopY), spectral databases and published assignment.

Data Processing and Multivariate Data Analysis:

The spectral data (from δ 0.2 to δ 9.5) were finally imported into Matlab software (version, the mathworks Inc, Natwick Mass.) and were transformed into 22K data-points. Resonance of water peak (δ 4.7-5.05) was removed from each spectrum in order to eliminate the variability linked to the water resonance presaturation. $^1$H NMR spectra were then normalized on total area and different multivariate statistics (PCA, OPLS, and OPLS-DA) were applied by using "unit variance" scaling.

Intermediates metabolites from host gut microbial co-metabolism, as well as from host β oxidation, BCAAs oxidation, Krebs's cycle and Nicotinamide adenine dinucleotide pathways assignable on urine $^1$H NMR spectra were integrated in order to assess the urinary excretion of these metabolites overtime for each individual animal for each group. Data were also analysed using multivariate analysis in combination with univariate analysis to select patterns associated with weight gain and group specificities.

Major Findings and Highlights:

Body Weight Gain Variability in C57BL/6J Mice Fed a HFD with or without Prebiotics.

Results on body weight (BW) and BW gain are very consistent. At day 7 already, BWs and BW gains in most of the prebiotics groups are significantly lower than in the high fat group and the difference increase until day 70 (FIG. 1). Nevertheless at the end of the study all the group are also significantly higher than the control group fed with a low fat diet. The time where this difference finally becomes significant differs from a prebiotic group to the other. Prebio 1 (inulin+FOS prebiotics) group is already higher on these parameters than Ctrl group at day 2 (BWG) or 35 (BW) and is very different at day 70 (BW 2.81 [1.19; 4.43] p=0.0023; BWG 2.46 [1.12; 3.81] p=0.0013).

Urine Metabolic Profiling Points Out Sustained Metabolic Signature Associated to High Fat Induced Obesity To investigate the specific metabolic signature associated with diet-induced obesity development, we acquired urine metabolic profiles overtime over a period of 13 weeks (FIG. 1). Urine metabolic profiles from mice fed with a low fat, high fat and high fat diet with prebiotics were then integrated with body weight and body weight gain. Based on this analysis using the full metabolic profiles, metabolic signatures could be ascribed to weight gain.

Figure 2:
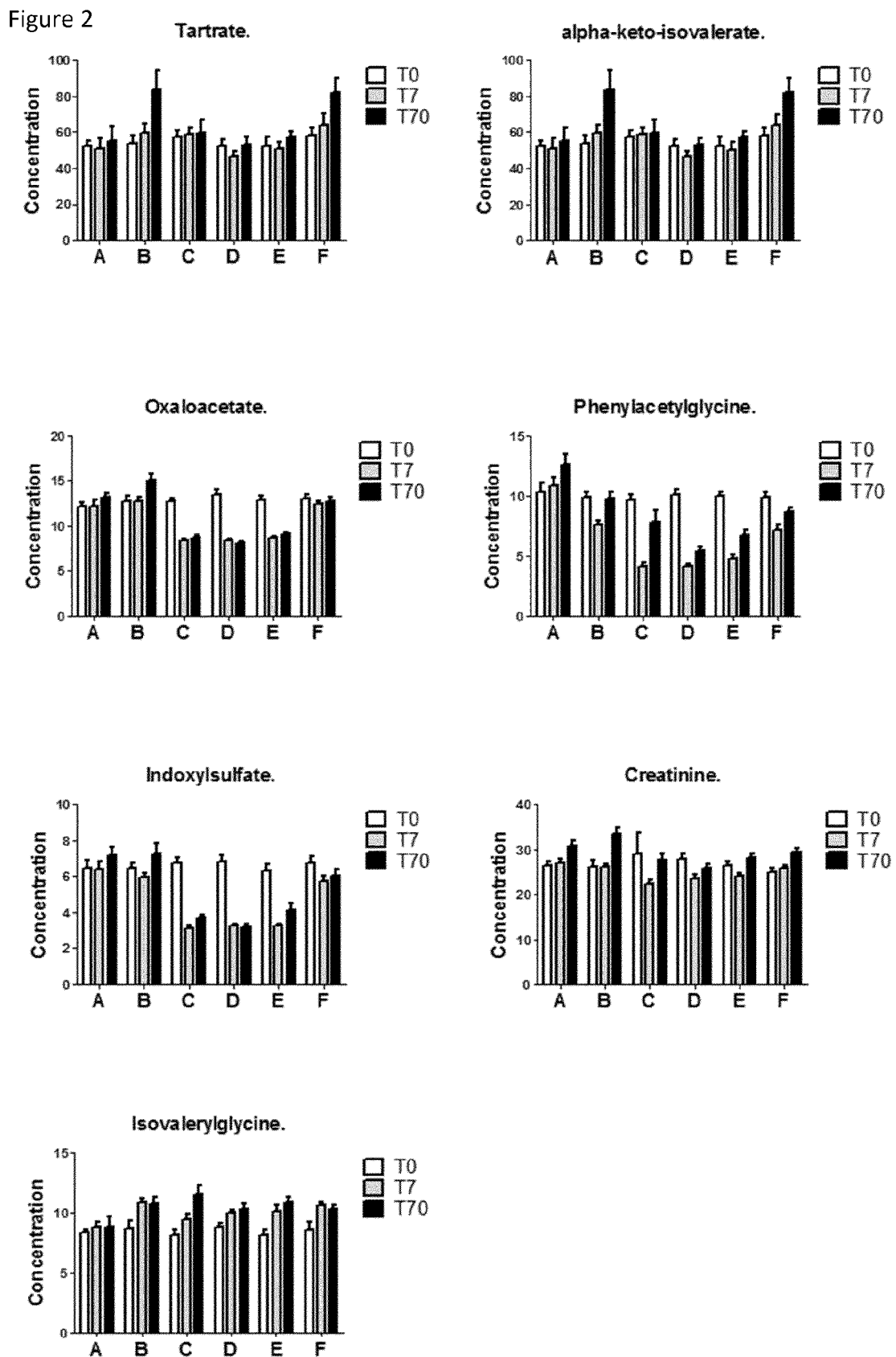
FIG. 2: Time dependent profiles of metabolites with specific response with prebiotic & related to weight gain. A: Controls; B: High Fat Controls, C: High fat GOS; D: High fat GOSCMOS, E: High fat Prebio1, F: High fat sugars. Vertical axis corresponds to the relative concentration in the metabolites as obtained by peak area integration, the data are given as area under the curve (AUC).
Figure 3:
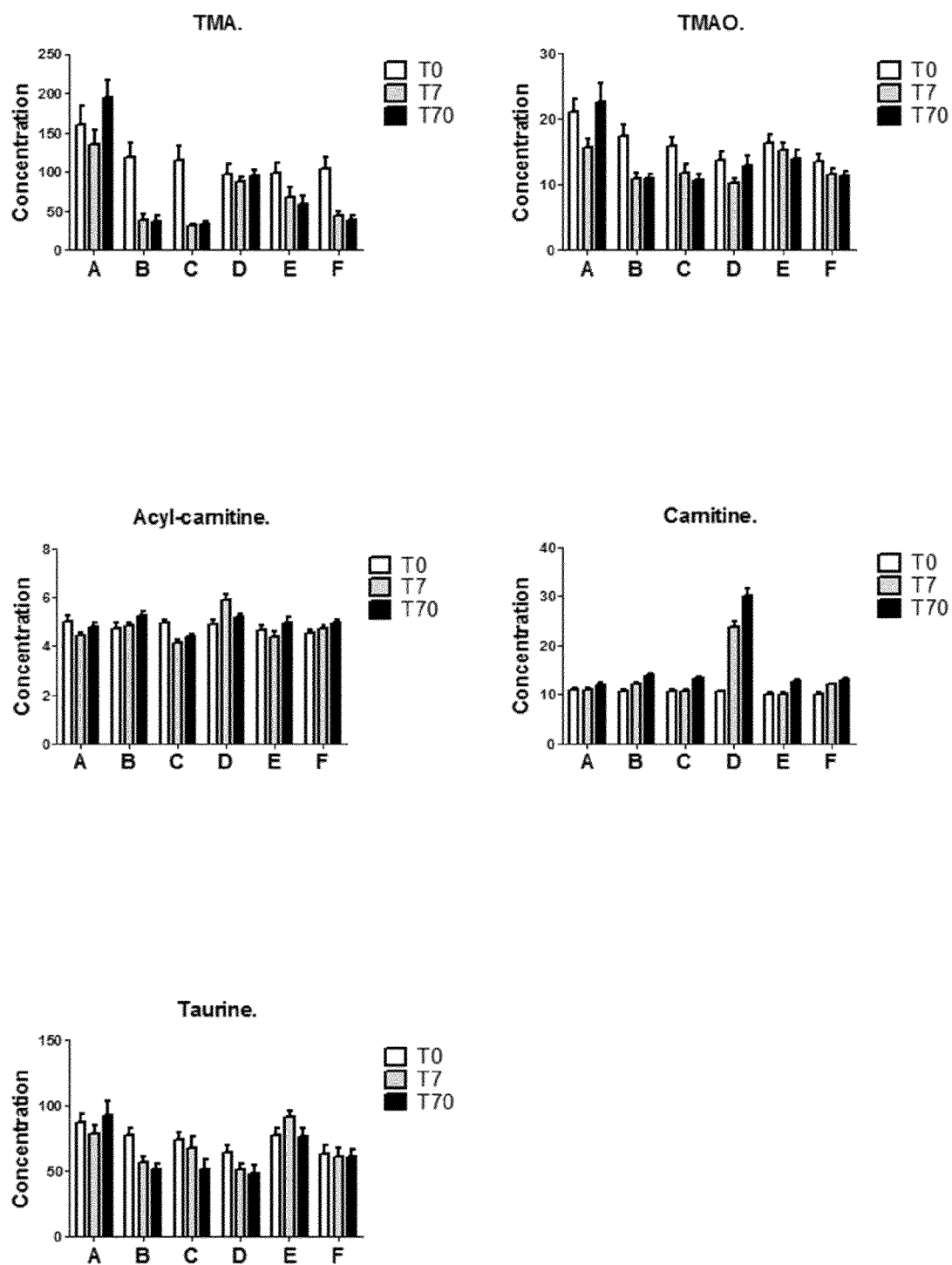
FIG. 3: Time dependent profiles of metabolites with specific response with prebiotic & related to weight gain. TMA, trimethylamine, TMAO, Trimethylamine-N-Oxide. A: Controls; B: High Fat Controls, C: High fat GOS; D: High fat GOSCMOS, E: High fat Prebio1, F: High fat sugars. Vertical axis corresponds to the relative concentration in the metabolites as obtained by peak area integration, the data are given as area under the curve (AUC).

Representative signals of the most influential metabolites were integrated and further analyses using multivariate data analysis was conducted using data at Day 0, Day 7 and Day 70 to identified the best early predictors of weight gain. Each model was calculated by using one predictive and several orthogonal components. The optimal number of orthogonal components was determined by $R^2Y$ and $Q^2Y$ goodness-of-fit statistics (FIG. 2). A first model was generated using 35 metabolites and then a second model was generated using the top 12 metabolites (as defined by Variable Importance Plot, and correlation coefficient values, FIGS. 2 and 3). For each model, the confusion matrix showed a very good model capacity for animal group stratification.

Metabolites with the highest correlation coefficient were identified, indicating the urinary metabolic variations encapsulates a modulation of both host and gut microbial metabolism. In particular, the level of carnitine, acylcarnitine, tricarboxylic acid metabolites, and the intermediates of branch chain amino acid oxidation were significantly correlated with weight gain. Conversely, the levels of methylamine derivatives produced from microbial choline metabolism (trimethylamine (TMA), and Trimethylamine (TMAO)) as well as taurine, were showing negative relationships with weight gain. Furthermore, the end-products of aromatic amino acid degradation by gut bacteria (phenylacetylglycine, indoxylsulfate) were also showing a positive linkage with weight gain.

Urine Metabolic Pattern of Metabolite Excretion Overtime Highlights a Specific Metabolic Adaptation Associated to Diet Induced Weight Gain and Prevention Using Prebiotics Application of similar data analyses for intra-group data modelling have revealed group specificities in term of host and gut microbial metabolic adaption, which may link to the beneficial reduction in body weight gain.

In particular, the degree of variation in the urinary level of gut microbial co-metabolites, including TMA, TMAO, phenylacetylglycine, indoxylsulfate, suggests a time- and nutrition dependent shift in the metabolic processing of dietary component by the gut microbiota. Whereas TMA and TMAO urinary levels are significantly reduced by high fat diet, the prebiotic supplementation tend to prevent the decreased production of TMA by the gut microbiota and further hepatic processing to TMAO. On the contrary, whilst indoxylsulfate and phenyacetylglycine urine concentration tends to be slightly decreased by the high fat diet, a greater reduction is observed with prebiotic supplementation. These observations taken together with the strong correlation with body weight gain, tend to illustrate that the efficacy of prebiotic modulation of the gut microbiota is essential to mediate the weight gain prevention benefit.

Hence, HFD treatment may imply significant changes in gut microbiota activity with it either prevented with prebiotic (TMA/TMAO) or compensated by other microbial processes such as proteolytic fermentation (phenylacetylglycine, indoxylsulfate).

In parallel, these gut microbial changes are associated with a significant modulation of the host central energy metabolism.

The excretion of isovalerylglycine and α-ketoisovalerate significantly and consistently increased in HFD fed group compared to LFD fed group overtime, so they constitute qualitative and stable candidate biomarkers of DIO. Prebiotic supplementation resulted in the prevention of these changes, as noted with a maintenance or slight decrease in the urinary level of α-ketoisovalerate, and a delayed increased in isovaleroylglycine. The latter change and similar concentrations being observed at Day 70 across groups with and without prebiotics, suggested that the overweight phenotype at day 70 induce a significant change in the energy metabolism. However, its delayed in the period of metabolic adaptation to diet switch seems to correlate with prebiotic efficacy in weight gain prevention. In addition, a similar transitory effect was also observed on the urinary excretion of creatinine, a well accepted marker of lean mass and muscle metabolism.

Moreover, the beneficial effect of prebiotics could be observed through the specific changes on tricarboxylic acid metabolic intermediate oxaloacetate and related tartrate, suggesting a modulation of energy production associated with a differential use of nutrient to fuel the body.

Finally, some specificities were observed in relation to carnitine and acylcarnitine metabolism, with inferred effect on fatty acid oxidation and mitochondrial metabolism, with a specific stimulation of the related physiological processed in animals received GOS-CMOS prebiotics.

Furthermore, in order to evaluate the relationship between early metabolic changes in urinary excretion of metabolites and weight gain, we calculated metabolite fold of change over the first week following diet switch, and compared the strength of the association to weight gain with relative metabolite concentration and its ratio to creatinine concentration (Table 1). The analysis showed some strong and consistent correlation between weight gain and the fold of change and relative concentration of the metabolites, including alpha-keto-isovalerate, indoxylsulfate, trimethalymine, phenylacetylglycine, oxaloacetate, and creatinine. In addition, the fold of changes are reported after one week and after 70 days of the high fat diet with and without prebiotics for each group and for the body weight gain (Table 2).

The above observations on the association of specific metabolites to weight gain, their specific modulation by prebiotics, and their identification as early metabolic indicators of response to prebiotic intervention, the biomarkers described herein allows the diagnosis of the likelihood to respond positively to prebiotic-based nutritional intervention for the prevention of diet induced weight gain.

The regulation of mitochondrial metabolism in HFD fed mice was previously investigated using a metabonomic approach. Urinary excretion of β oxidation intermediates: hexanoylglcyine, carnitine and acylcarnitine were consistently increased in urine of HF fed mice compared to LF fed mice, which suggests an increase of fatty acid overflow in the mictochondria and an activation of β oxidation. In the present study, prebiotics tend to promote a further increase in these metabolic processes, suggesting a more efficient oxidation of fatty acid, which is maintained over time.

Leucine, valine, isoleucine as well as intermediates of BCAAs catabolism (isovalerylglycine, α-keto-βmethylvalerate and α-ketoisovalerate) were significantly and consistently increased in HF fed mice supporting the hypothesis of HFD associated up-regulation of BCAAs catabolism. In the present study, the prebiotics tend to prevent the specific increase in isoleucine catabolism as noted with the maintenance of normal levels of alpha-keto-iso-valerate.

Valine and isoleucine catabolism may be up-regulated in HF fed mice inducing the formation of succinyl-CoA and the production of the following Krebs's cycle intermediates. Surprisingly, the other Krebs's cycle intermediates (citrate, cis-aconitase, α-ketoglutarate) were not significantly different between LF and HF fed mice suggesting a disconnection between leucine catabolism and beta oxidation producing acetyl-CoA, and Krebs's cycle. Specific metabolic regulations could divert the flux of acetyl-CoA toward other metabolic pathways. These results confirm that HFD induces an up-regulation of mitochondrial oxidative pathways and Krebs's cycle which might lead to an increase of energy production. In the present study, prebiotics tend to induce a deep modulation of Krebs' cycle intermediates with suggests a differential metabolism of mitochondrial oxidative pathways.

Finally, the current findings showed that prebiotic modulation of gut microbial activities and subsequently the further metabolism by the host of the derived products, may be essential in mediating the benefits for weight gain. Moreover, the early metabolic adaptation to the diet changes seems to correlate with the final acquired metabolic and anthropometric phenotype of the animals, making gut microbial related metabolites key markers for future personalized weight management nutritional solutions.

Additional Embodiments

In further aspects, the present invention provides embodiments as described in the following numbered paragraphs.

1. A method for predicting and/or quantifying the response of a subject to prebiotics in the prevention of diet induced weight gain, comprising
  a) determining a level of trimethylamine in a urine sample obtained from a subject that has consumed prebiotics, and
  b) comparing the subject's trimethylamine level to a predetermined reference value,
  wherein an increased trimethylamine level, or an absence of change in the trimethylamine level, in the urine sample compared to the predetermined reference value indicates that the administration of prebiotics is effective in the prevention of diet induced weight gain in the subject.

2. A method for predicting and/or quantifying the response of a subject to prebiotics in the prevention of diet induced weight gain, comprising
  a) determining a level of alpha-keto-isovalerate in a urine sample obtained from a subject that has consumed prebiotics, and
  b) comparing the subject's alpha-keto-isovalerate level to a predetermined reference value,
  wherein a decreased alpha-keto-isovalerate level, or an absence of change in the alpha-keto-isovalerate level, in the urine sample compared to the predetermined reference value indicates that the administration of prebiotics is effective in the prevention of diet induced weight gain in the subject.

3. The method of paragraph 1 or paragraph 2, wherein the diet is a high fat diet.

4. The method of any preceding paragraph, further comprising the steps of
  a) determining the level of at least one further biomarker selected from the group consisting of trimethylamine, oxaloacetate, creatinine, indoxyl sulfate and alpha-keto-isovalerate in the urine sample, and
  b) comparing the subject's level of the at least one further biomarker to a predetermined reference value,
    wherein:
    (i) a decreased oxaloacetate, creatinine, indoxyl sulfate and/or alpha-keto-isovalerate level, or an absence of change in the oxaloacetate, creatinine, indoxyl sulfate and/or alpha-keto-isovalerate level, in the urine sample; and/or (ii) an increased trimethylamine level, or an absence of change in the trimethylamine level, in the urine sample;

compared to the predetermined reference values indicates that the administration of prebiotics will be effective in the prevention of diet induced weight gain in the subject.

5. The method according to any preceding paragraph, wherein the levels of the biomarkers in the urine sample are determined by 1H-NMR and/or mass spectrometry.

6. The method according to any preceding paragraph, wherein the predetermined reference value is based on an average trimethylamine level and/or alpha-keto-isovalerate in urine in a control population of subjects consuming a high fat diet.

7. The method according to any of paragraphs 1 to 5, wherein the predetermined reference value is the trimethylamine level and/or alpha-keto-isovalerate level in urine in the subject before the prebiotics were consumed.

8. The method according to any preceding paragraph, wherein the level of trimethylamine, alpha-keto-isovalerate and/or the further biomarkers are determined in a urine sample obtained from the subject after at least three consecutive days of prebiotic consumption.

9. The method according to any preceding paragraph, wherein the prebiotic is selected from the group consisting of oligosaccharides, optionally containing fructose, galactose, mannose; dietary fibers, in particular soluble fibers, soy fibers; inulin; or mixtures thereof.

10. The method according to paragraph 9, wherein the prebiotics are selected from the group consisting of fructo-oligosaccharides (FOS); galacto-oligosaccharides (GOS); isomalto-oligosaccharides; xylo-oligosaccharides; bovine milk oligosaccharides (BMOS); glycosylsucrose (GS); lactosucrose (LS); lactulose (LA); palatinose-oligosaccharides (PAO); malto-oligosaccharides (MOS); gums and/or hydrolysates thereof; pectins and/or hydrolysates thereof; and combinations thereof.

11. The method of paragraph 10, wherein the prebiotics comprise (a) galactooligosaccharides (GOS) (b) bovine milk oligosaccharides (BMOS) or (c) inulin and fructooligosaccharides (FOS).

12. The method of paragraph 11, wherein the bovine milk oligosaccharides (BMOS) comprise cow's milk oligosaccharides-galactooligosaccharides (CMOS-GOS).

13. The method according to any preceding paragraph, wherein the subject has consumed the prebiotics in an amount of at least 2 g/day.

14. The method according to any preceding paragraph, wherein the subject is a mammal such as a human; a non-human species, including a primate; a livestock animal such as a sheep, a cow, a pig, a horse, a donkey, or a goat; a laboratory test animals such as mice, rats, rabbits, guinea pigs, or hamsters; or a companion animal such as a dog or a cat.

15. The method according to any preceding paragraph, wherein the method is used to devise a stratified diet for a group of subjects or a personalized diet for the subject.

16. A method for preventing diet-induced weight gain in a subject, comprising:

a) performing a method as described in any of paragraphs 1 to 15; and b) administering prebiotics to the subject if (i) the level of trimethylamine in the urine sample is increased or unchanged and/or (ii) the level of alpha-keto-isovalerate in the urine sample is decreased or unchanged, compared to the predetermined reference value.

17. A method according to paragraph 16, wherein administration of prebiotics to the subject is continued for at least one month.

18. A method according to paragraph 16, wherein if (i) the level of trimethylamine in the urine sample is decreased or unchanged and/or (ii) the level of alpha-keto-isovalerate in the urine sample is increased or unchanged, compared to the predetermined reference sample, prebiotics are not administered to the subject.

19. A method according to paragraph 18, wherein an alternative treatment for weight gain prevention is provided to the subject, the treatment selected from calorie restriction, dietary fat intake reduction, a non-prebiotic weight loss product, or an exercise program.

20. A biomarker in urine for predicting and/or quantifying the response of subjects to prebiotics in the prevention of diet induced weight gain, wherein the biomarker is trimethylamine.

21. A biomarker in urine for predicting and/or quantifying the response of subjects to prebiotics in the prevention of diet induced weight gain, wherein the biomarker is alpha-keto-isovalerate.

22. Use of trimethylamine as a biomarker in urine for predicting and/or quantifying the response of subjects to prebiotics in the prevention of diet induced weight gain.

23. Use of alpha-keto-isovalerate as a biomarker in urine for predicting and/or quantifying the response of subjects to prebiotics in the prevention of diet induced weight gain.

Although the invention has been described by way of example, it should be appreciated that variations and modifications may be made without departing from the scope of the invention as defined in the claims. Furthermore, where known equivalents exist to specific features, such equivalents are incorporated as if specifically referred to in this specification. Further advantages and features of the present invention are apparent from the figures and non-limiting examples.

Those skilled in the art will understand that they can freely combine all features of the present invention disclosed herein. In particular, features described for different embodiments of the present invention may be combined.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

TABLE 1

Summary of relationships between metabolites and weight gain in high fat induced weight gain

| | Correlation Coefficient with Weight Gain in high fat fed animals (r value) | | |
|---|---|---|---|
| Metabolites | Fold of change (T7/T0) | Concentration T7 | Ratio metabolite/ creatinine T7 |
| Acyl.carnitine | 0.158253393 | 0.098288017 | −0.139618561 |
| Carnitine | −0.138725606 | −0.129539973 | −0.216813487 |
| Creatinine | 0.306373827 | 0.402834663 | Not applicable |
| Indoxylsulfate | 0.655850247 | 0.680973297 | 0.607275477 |
| Isovalerylglycine | 0.153748589 | 0.307939099 | 0.005581991 |
| Oxaloacetate | 0.729067593 | 0.750868285 | 0.659882916 |
| Phenylacetylglycine | 0.525457288 | 0.574980126 | 0.498217971 |
| Tartrate | 0.018061809 | 0.273162626 | 0.127048017 |

TABLE 1-continued

Summary of relationships between metabolites and weight gain in high fat induced weight gain

| Metabolites | Correlation Coefficient with Weight Gain in high fat fed animals (r value) | | |
|---|---|---|---|
| | Fold of change (T7/T0) | Concentration T7 | Ratio metabolite/ creatinine T7 |
| Taurine | −0.15540473 | −0.275405566 | −0.339707993 |
| TMA | −0.235079974 | −0.24950404 | −0.282660746 |
| TMAO | −0.058723531 | −0.208883241 | −0.300038561 |
| Alpha-keto-isovalerate | 0.375628295 | 0.392090066 | 0.061032612 |

TABLE 2

Summary of the fold of changes in selected metabolites over time in animals fed with a high fat diet with and without prebiotics

| Metabolite | Group | Fold of change (T7-T0) | Fold of change (T70-T0) |
|---|---|---|---|
| Body weight gain | Low Fat control | 1.0 ± 0.0 | 1.1 ± 0.1 |
| | High fat control | 1.1 ± 0.0 | 1.6 ± 0.2 |
| | High fat & GOS | 1.1 ± 0.0 | 1.2 ± 0.1 |
| | High fat & GOSCMOS | 1.1 ± 0.0 | 1.3 ± 0.1 |
| | High Fat & Prebio1 | 1.1 ± 0.0 | 1.2 ± 0.1 |
| | High fat & lactose | 1.1 ± 0.0 | 1.4 ± 0.1 |
| Acyl.carnitine | Low Fat control | 93.3 ± 26 | 95.7 ± 21.4 |
| | High fat control | 108 ± 15.3 | 112.4 ± 13.8 |
| | High fat & GOS | 84.8 ± 11.6 | 88.9 ± 11 |
| | High fat & GOSCMOS | 126 ± 15.9 | 109.2 ± 17.3 |
| | High Fat & Prebio1 | 96.2 ± 28.1 | 108.3 ± 29.8 |
| | High fat & lactose | 105 ± 14.8 | 112.2 ± 16.1 |
| Carnitine | Low Fat control | 101.8 ± 18.6 | 110.4 ± 16 |
| | High fat control | 115.9 ± 14.1 | 130.9 ± 17.9 |
| | High fat & GOS | 102.1 ± 13.4 | 122.9 ± 13.6 |
| | High fat & GOSCMOS | 226.2 ± 33.3 | 293.6 ± 39.4 |
| | High Fat & Prebio1 | 101.7 ± 9.6 | 127 ± 13.6 |
| | High fat & lactose | 119.7 ± 8.6 | 132.2 ± 14.1 |
| Creatinine | Low Fat control | 104.4 ± 18.7 | 118.5 ± 19.5 |
| | High fat control | 100.3 ± 17.4 | 131.4 ± 27.3 |
| | High fat & GOS | 86.8 ± 24.1 | 109.8 ± 30.9 |
| | High fat & GOSCMOS | 87.1 ± 10.8 | 93.1 ± 15.1 |
| | High Fat & Prebio1 | 91.6 ± 10.9 | 107.6 ± 17.1 |
| | High fat & lactose | 106.2 ± 16 | 125.4 ± 18 |
| Indoxylsulfate | Low Fat control | 99.6 ± 26 | 119.8 ± 34.6 |
| | High fat control | 96.1 ± 23.7 | 118.3 ± 49.8 |
| | High fat & GOS | 46.7 ± 9.4 | 56.1 ± 11.4 |
| | High fat & GOSCMOS | 50.8 ± 12.1 | 48.9 ± 10.6 |
| | High Fat & Prebio1 | 54.6 ± 16.8 | 68 ± 21.7 |
| | High fat & lactose | 86.7 ± 23.9 | 99 ± 32.3 |
| Isovaleryl-glycine | Low Fat control | 105.4 ± 18.8 | 106.8 ± 42.5 |
| | High fat control | 128 ± 30.4 | 131.3 ± 38.2 |
| | High fat & GOS | 118.2 ± 28.2 | 143.5 ± 45.2 |
| | High fat & GOSCMOS | 116.5 ± 16.5 | 116.1 ± 18.3 |
| | High Fat & Prebio1 | 129.1 ± 28.6 | 137.7 ± 24.4 |
| | High fat & lactose | 130.2 ± 24.2 | 125.7 ± 25.8 |
| Oxaloacetate | Low Fat control | 101.1 ± 24.7 | 111.9 ± 19.4 |
| | High fat control | 103.2 ± 18.4 | 120.7 ± 30.7 |
| | High fat & GOS | 66.2 ± 7.6 | 68.8 ± 7.7 |
| | High fat & GOSCMOS | 64.6 ± 8.4 | 59.3 ± 7.9 |
| | High Fat & Prebio1 | 69.5 ± 12.5 | 71.9 ± 13 |
| | High fat & lactose | 95.2 ± 14.7 | 102.3 ± 17.5 |
| Phenylacetyl-glycine | Low Fat control | 107.2 ± 20.2 | 128.9 ± 34.8 |
| | High fat control | 77.7 ± 15.6 | 102.3 ± 28.5 |
| | High fat & GOS | 41.8 ± 8.6 | 82.7 ± 36.4 |
| | High fat & GOSCMOS | 42.5 ± 10.3 | 55.2 ± 17.7 |
| | High Fat & Prebio1 | 50.4 ± 23.3 | 69.3 ± 27.6 |
| | High fat & lactose | 72.4 ± 15 | 91.5 ± 14.8 |
| Tartrate | Low Fat control | 94.6 ± 36.3 | 114 ± 72.8 |
| | High fat control | 123.1 ± 40.3 | 172.4 ± 104 |
| | High fat & GOS | 117 ± 60.8 | 117.4 ± 84.3 |
| | High fat & GOSCMOS | 95.3 ± 38.1 | 111.2 ± 46.9 |
| | High Fat & Prebio1 | 123 ± 111.7 | 139.7 ± 103.4 |
| | High fat & lactose | 115.3 ± 52 | 150.5 ± 62.9 |
| Taurine | Low Fat control | 90.8 ± 24.6 | 117.1 ± 69.1 |
| | High fat control | 81.9 ± 39.6 | 72.6 ± 33.2 |
| | High fat & GOS | 93.1 ± 45.4 | 75.1 ± 46.1 |
| | High fat & GOSCMOS | 86.1 ± 45.9 | 89.4 ± 46.3 |
| | High Fat & Prebio1 | 127.3 ± 53.6 | 104.6 ± 40.5 |
| | High fat & lactose | 120.8 ± 68.1 | 129.9 ± 87.8 |
| Trimethyl-amine (TMA) | Low Fat control | 134.1 ± 138.4 | 160.6 ± 170.9 |
| | High fat control | 45.6 ± 35 | 44.5 ± 38.4 |
| | High fat & GOS | 37.8 ± 23.9 | 39.7 ± 23 |
| | High fat & GOSCMOS | 118.7 ± 78.7 | 125.5 ± 57.9 |
| | High Fat & Prebio1 | 94.5 ± 74.4 | 106 ± 122.4 |
| | High fat & lactose | 62.6 ± 53.5 | 51.6 ± 38.1 |
| Trimethyl-amine-N-Oxide (TMAO) | Low Fat control | 83.7 ± 34.8 | 122.2 ± 73.2 |
| | High fat control | 80.1 ± 40.1 | 72.5 ± 31.4 |
| | High fat & GOS | 79.3 ± 41.1 | 74.3 ± 36.8 |
| | High fat & GOSCMOS | 82.4 ± 39.9 | 110.6 ± 58.7 |
| | High Fat & Prebio1 | 101.2 ± 39.3 | 94.4 ± 43.3 |
| | High fat & lactose | 101.4 ± 50.7 | 98.5 ± 44.6 |
| Alpha-ketoiso-valerate | Low Fat control | 106.8 ± 10.3 | 94.8 ± 15 |
| | High fat control | 150.4 ± 26.1 | 119.7 ± 20.7 |
| | High fat & GOS | 124.1 ± 20.6 | 124.4 ± 21 |
| | High fat & GOSCMOS | 132 ± 14.3 | 120 ± 17.3 |
| | High Fat & Prebio1 | 126 ± 23.9 | 125.1 ± 18.1 |
| | High fat & lactose | 147.6 ± 15.7 | 126.8 ± 13.7 |

The invention claimed is:

1. A method for predicting and/or quantifying the response of a subject to prebiotics in the prevention of diet induced weight gain, comprising:
   a) determining a level of indoxyl sulfate in a urine sample obtained from a subject that has consumed prebiotics using $^1$H-NMR spectroscopy or mass spectroscopy, and
   b) comparing the subject's indoxyl sulfate level to a predetermined reference value by mapping or graphing the urinary excretion of indoxyl sulfate,
   wherein a decreased indoxyl sulfate level, or an absence of change in the indoxyl sulfate level, in the urine sample compared to the predetermined reference value indicates that the administration of prebiotics is effective in the prevention of diet induced weight gain in the subject,
   and wherein the predetermined reference value is based on an average indoxyl sulfate level in a control population of subjects consuming a high fat diet and the change of indoxyl sulfate level is determined relative to a cut-off value.

2. The method of claim 1, wherein the diet is a high fat diet.

3. The method of claim 1, further comprising the steps of
   a) determining the level of at least one further biomarker selected from the group consisting of oxaloacetate, creatinine, trimethylamine, and alpha-keto-isovalerate in the urine sample, and b) comparing the subject's level of the at least one further biomarker to a predetermined reference value, wherein:
  (i) a decreased oxaloacetate, creatinine, and/or alpha-keto-isovalerate level, or an absence of change in the oxaloacetate, creatinine, and/or alpha-keto-isovalerate level, in the urine sample; and/or
  (ii) an increased trimethylamine level, or an absence of change in the trimethylamine level, in the urine sample;

compared to the predetermined reference values indicates that the administration of prebiotics will be effective in the prevention of diet induced weight gain in the subject.

4. The method according to claim 1, wherein the predetermined reference value is the indoxyl sulfate level in urine in the subject before the prebiotics were consumed.

5. The method according to claim 1, wherein the level of indoxyl sulfate and/or the further biomarkers are determined in a urine sample obtained from the subject after at least three consecutive days of prebiotic consumption.

6. The method according to claim 1, wherein the prebiotic is selected from the group consisting of oligosaccharides, optionally containing fructose, galactose, mannose; dietary fibers, in particular soluble fibers, soy fibers; inulin; or mixtures thereof.

7. The method according to claim 6, wherein the prebiotics are selected from the group consisting of fructo-oligosaccharides (FOS); galacto-oligosaccharides (GOS); isomalto-oligosaccharides; xylo-oligosaccharides; bovine milk oligosaccharides (BMOS); glycosylsucrose (GS); lactosucrose (LS); lactulose (LA); palatinose-oligosaccharides (PAO); malto-oligosaccharides (MOS); gums and/or hydrolysates thereof; pectins and/or hydrolysates thereof; and combinations thereof.

8. The method of claim 7, wherein the prebiotics comprise (a) galactooligosaccharides (GOS) (b) bovine milk oligosaccharides (BMOS) or (c) inulin and fructooligosaccharides (FOS).

9. The method of claim 8, wherein the bovine milk oligosaccharides (BMOS) comprise cow's milk oligosaccharides-galactooligosaccharides (CMOS-GOS).

10. The method according to claim 1, wherein the subject has consumed the prebiotics in an amount of at least 2 g/day.

11. The method according to claim 1, wherein the subject is a mammal such as a human; a non-human species, including a primate; a livestock animal such as a sheep, a cow, a pig, a horse, a donkey, or a goat; a laboratory test animals such as mice, rats, rabbits, guinea pigs, or hamsters; or a companion animal such as a dog or a cat.

12. The method according to claim 1, wherein the method is used to devise a stratified diet for a group of subjects or a personalized diet for the subject.

13. A method for preventing diet-induced weight gain in a subject, comprising:
  a) performing a method as described in claim 1; and
  b) administering prebiotics to the subject if the level of indoxyl sulfate in the urine sample is decreased or unchanged compared to the predetermined reference value.

14. A method according to claim 13, wherein administration of prebiotics to the subject is continued for at least one month.

15. A method according to claim 13, wherein if the level of indoxyl sulfate in the urine sample is increased compared to the predetermined reference sample, prebiotics are not administered to the subject.

16. A method according to claim 15, wherein an alternative treatment for weight gain prevention is provided to the subject, the treatment selected from calorie restriction, dietary fat intake reduction, a non-prebiotic weight loss product, or an exercise program.

* * * * *